United States Patent
Ishii

(10) Patent No.: US 6,396,945 B1
(45) Date of Patent: May 28, 2002

(54) IMAGE DEFECT DETECTION APPARATUS AND METHOD

(75) Inventor: Toshiyuki Ishii, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/218,104

(22) Filed: Dec. 22, 1998

(30) Foreign Application Priority Data

Dec. 25, 1997 (JP) ............................................. 9-356565

(51) Int. Cl.⁷ ................................................ G06K 9/00
(52) U.S. Cl. ........................ 382/149; 382/144; 382/256
(58) Field of Search ................................. 382/141–149, 382/150, 151, 152, 254, 256, 257; 356/237

(56) References Cited

U.S. PATENT DOCUMENTS

| | | | |
|---|---|---|---|
| 4,587,617 A | * 5/1986 | Barker et al. | 382/149 |
| 4,590,607 A | * 5/1986 | Kauth | 382/257 |
| 4,644,585 A | * 2/1987 | Crimmins et al. | 382/257 |
| 5,046,113 A | 9/1991 | Hoki | 382/8 |
| 5,808,735 A | * 9/1998 | Lee et al. | 356/237 |

FOREIGN PATENT DOCUMENTS

| | | |
|---|---|---|
| JP | 62-259184 | 11/1987 |
| JP | 5-89223 | 4/1993 |
| JP | 5-90367 | 4/1993 |
| JP | 5-107195 | 4/1993 |

* cited by examiner

Primary Examiner—Joseph Mancuso
Assistant Examiner—Vikkram Bali
(74) Attorney, Agent, or Firm—Sughrue Mion, PLLC

(57) ABSTRACT

An image defect detection apparatus comprises a means to prepare two replicates of inspection image from a single inspection image, the first image processing means to process an image applying the expansion filter and the contraction filter in such order for the one of replicated inspection images, the second processing means to process an image using the contraction filter and the expansion filter in such order for the other of replicated digital image information, and an image information outputting means to output image information composed of the differential value respectively outputted from the first image processing means and the second image processing means.

26 Claims, 10 Drawing Sheets

| P(x-1,y-1) | P(x,y-1) | P(x+1,y-1) | ~21 |
| --- | --- | --- |
| P(x-1,y) | P(x,y) | P(x+1,y) |
| P(x-1,y+1) | P(x,y+1) | P(x+1,y+1) |

P(X+i,Y+j) IS A BRIGHTNESS (i,j=-1,0,1)
EXPANSION FILTER: $P(x,y) = \max_{i,j=-1,0,1}\{P(x+i,y+j)\}$
CONTRACTION FILTER: $P(x,y) = \min_{i,j=-1,0,1}\{P(x+i,y+j)\}$

FIG. 2

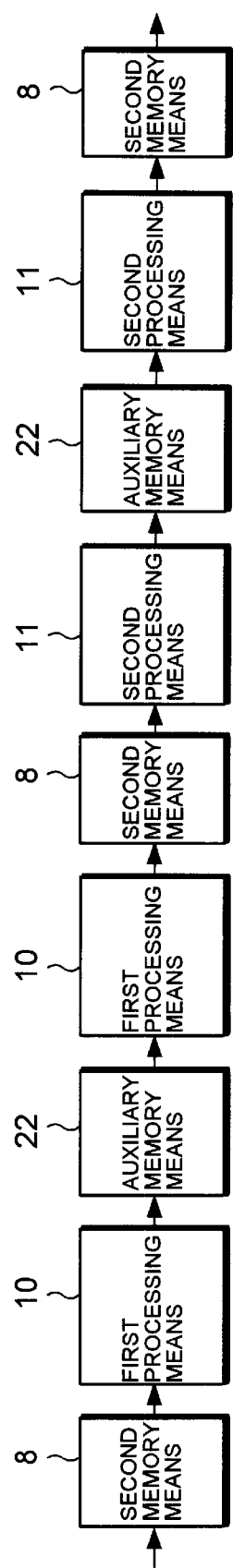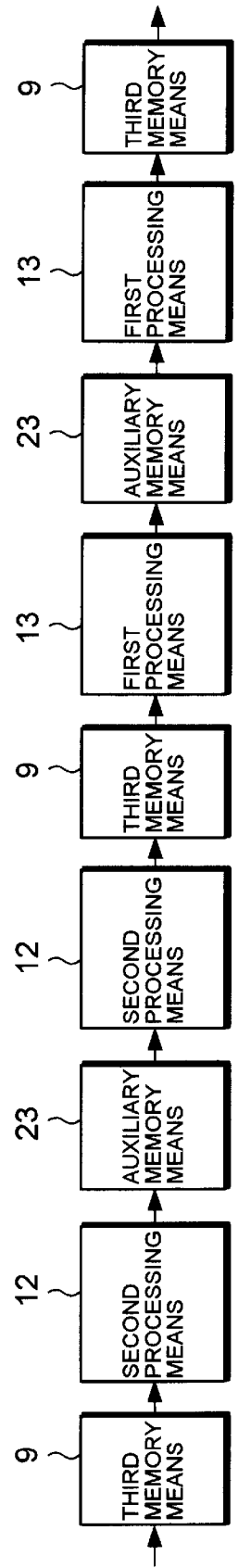

IMAGE DEFECT DETECTION APPARATUS AND METHOD

BACKGROUND OF THE INVENTION (i) Field of the Invention

The present invention relates to an image defect detection apparatus and method, particularly relates to an image defect detection apparatus and method for detecting a defect in the images of photomasks (reticles) and the like.

(ii) Description of the Related Art

Conventionally, there are two image defect detection methods using image processing to inspect a photomask (reticle), etc. used in the semiconductor device manufacturing process. The one is the die-to-die for comparison of same patterns in different positions in real patterns and the other is the die-to-database for comparison of a real pattern with a designed pattern (usually, CAD data). These methods are shown for example in Japanese Patent Application Laid-Open No. 10463/1996 or Japanese Patent Application Laid-Open No. 76359/1996. However, in consideration of future miniaturization of photomasks patterns, there are problems in inspecting them by said two inspection methods. When a pattern is different in size from another pattern of the different position on the same photomask, even though the level of the difference is negligible in the inspection, the pattern is judged as a defect in the die-to-die.

Usually in the die-to-die, the sensitivity of inspection should be suppressed to prevent a false defect(a seeming defect occurred by inaccurate inspection of a product to be passed in a test) caused by the dispersion of products to be passed in a test, because respective patterns existing in distant positions on the same photomask are compared each other.

On the other hand, in the die-to-database, a pattern image should be generated from a designed data to compare the designed data with a real pattern image. The false defect occurs, if the pattern image generated from the designed data is not very coincident with the real pattern image.

In the real pattern image, there is the dispersion of products to be passed in a test on the same photomask as shown above. This means that somewhat different spots occur by said reason, if an image is generated from a designed data based on a pattern.

In addition, regardless of the die-to-die and the die-to-database, the reproducibility of an image is not satisfactory because of an effect of vibration, etc. of a stage carrying a photomask an optical device for sensing in processes before the collection of the image.

In the recent years, the size of a defect—necessary in detection—has gradually become smaller according to miniaturization of a pattern. Particularly, image defect based on a size or an image defect based on a position increasingly become difficult to detect.

Another image defect detection apparatus and method has been described in Japanese Patent Application Laid-Open No. 200372/1983. However, the art described in that is only a method of compressing a digital image information to simplify the conversion treatment circuit in the image processing, and a method to detect an image defect has not been disclosed.

In addition, in Japanese Patent Application Laid-Open Nos. 215118/1990 and 249656/1995, an mask inspection apparatus and method has been disclosed. However, a use of transmitted rays has been only described; a method for enlargement and reduction of an image has not been described.

Further, in Japanese Patent Application Laid-Open No. 76359/1996, the combined use of transmitted rays and reflected rays in the inspection of a mask has been described, and in Japanese Patent Application Laid-Open No. 304997/1996, a method for comparison of each image datum, that was made by enlarging and reducing one image datum of two image data, with the other image datum in image inspection. However, cancellation of an error caused by an effect of an optical error, vibration, etc. is impossible by this method.

SUMMARY OF THE INVENTION

It is an object of the present invention to provide a speedy and precise image defect detecting apparatus and method which can judge negligible difference in size of a products, such as photomask (reticle) and the like, by improving a defect of said conventional arts.

The present invention adopts the constitution of arts described below in order to achieve the above object.

The first aspect of the present invention is an image defect detection apparatus comprising a means to make two copied inspection images from a single inspection image, the first image processing means to carry out image processing applying an expansion filter and a contraction filter in the order to the one copied inspection image, the second image processing means to carry out image processing applying a contraction filter and an expansion filter in the order to the other copied inspection image, and a means to output image information made from differential values of image information outputted from said respective first image processing means and second image processing means.

The second aspect of the present invention is a image defect detection apparatus comprising a data conversion means to convert the inspection image to digital image information, the first memory means to store said digital image information outputted from said data conversion means, the second memory means and the third memory means copying digital image information—stored by said first memory means—to store individually, the first processing means to execute the first process by using an expansion filter for digital image information stored by said second memory means, the second processing means to execute the second process by using a contraction filter for digital image information yielded from the result of computing by the first processing means, the third processing means to execute the second process by using a contraction filter for digital image information stored by said third memory means, the fourth processing means to execute the first process by using the expansion filter for digital image information yielded from the result of computing by the third processing means, the fifth processing means to compute the differential values of respective sets of digital image information yielded from the results of computing by the second processing means and the fourth processing means, and the fourth memory means to store the result of computation by the fifth processing means.

The third aspect of the present invention is a image defect detection method determining presence or absence of an image defect in a given inspection image, wherein at least two image copies are made from the digital image information of the inspection image obtained by digital processing of the inspection image, the first processing information is yielded by processing the first processing means using the expansion filter and the second processing means using the contraction filter in such order for the one copied digital image information, and also the second processing information is yielded by processing the second processing means using the contraction filter and the first processing means using the expansion filter in such order for the one copied digital image information, and from the result the differential values of the first processing information and the second processing information are computed, and presence or absence of an image defect in the inspection image.

BRIEF DESCRIPTION OF THE DRAWINGS

FIG. 2 is a figure showing of an embodiment of spatial filter used for an image defect detection apparatus of the present invention.

FIG. 3(A) and FIG. 3(B) are flow chart showing of an embodiment of operation procedure in an image defect detection method of the present invention.

FIG. 7(A) is a pattern obtained by the first processing for the image pattern of the FIG. 6, and FIG. 7(B) is a pattern obtained by the second processing for the image pattern of the FIG. 7(A)

FIG. 8(A) is a pattern obtained by the second processing for the image pattern of the FIG. 6, and FIG. 8(B) is a pattern obtained by the first processing for the image pattern of the FIG. 8(A)

DETAILED DESCRIPTION OF THE PREFERRED EMBODIMENTS

The image defect detection apparatus and method of the present invention has said constitution of art, and allows speedy inspection without any effect of dispersion—a cause of occurrence of a false defect, for example, in inspection of a photomask (reticle) used in the semiconductor device manufacturing process—of products passed in a test.

In the present invention, an inputted image is respectively reproduced (copied) in two memories, contradictory filter processing is carried out for these two images arbitrary times, a differential image is made from these two images, a pixel showing a threshold or higher value, if it is evaluated as a defect in the differential image, is determined as a defect, and finally the objective part of the original image taken is displayed on a monitor, etc.

This means that a problem of the dispersion of products to be passed in a test is negligible in the present invention, because the two images finally compared are originally identical images. In addition in the present invention, it is unnecessary to position (align) precisely—like that performed in the die-to-die and the die-to-database—two different images such as comparative image and reference image immediate before the inspection, because two images are made from the identical inputted image. Further, the inspection algorithms of the present invention are made from a combination of simple filtering processes to improve the inspecting speed compared with a conventional inspection apparatus.

The following is detailed description of embodiments of an image defect detection apparatus of the present invention with reference to drawings.

Figure 1:
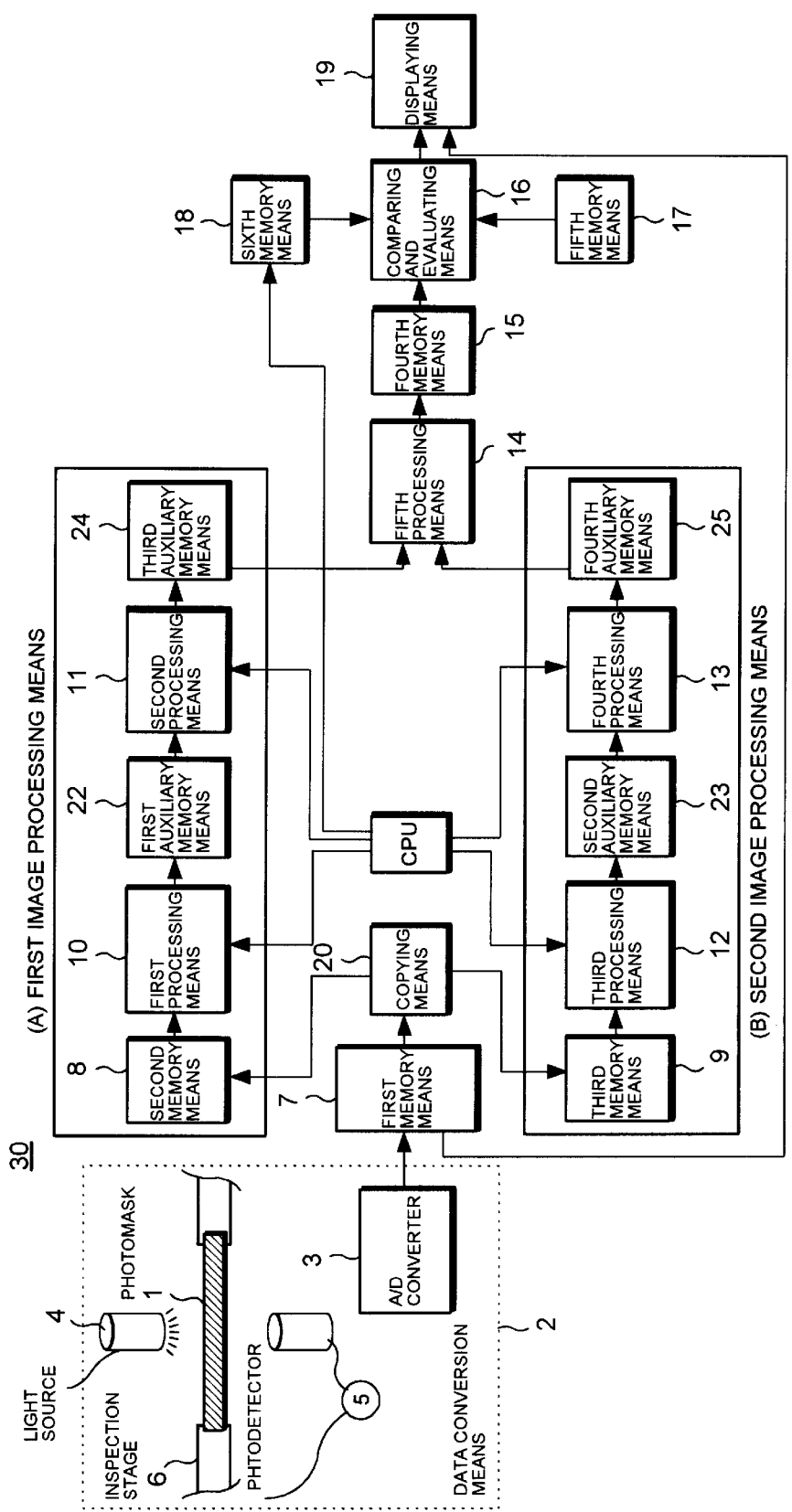
FIG. 1 is a block diagram showing the constitution of an embodiment of an image defect detecting apparatus of the present invention.

Referring now to FIG. 1 of the drawing, a block diagram showing the constitution of an embodiment of an image defect detecting apparatus 30 of the present invention is depicted.

The figure shows the image defect detection apparatus 30 characterized by comprising a data conversion means 2 to convert inspection image of the inspection object, such as photomask 1 to digital image information, the first memory means 7 to store the digital image information outputted from the data conversion means 2, the second memory means 8 and third memory means 9 to store individually the digital image information stored in the first memory means 7 by copying, the first processing means 10 to execute the first process by using an expansion filter for the digital image information stored in the second memory means 8, the second processing means 11 to execute the second process by using a contraction filter for digital image information yielded from the result of computing by the first processing means 10, the third processing means 12 to execute the second process by using a contraction filter for digital image information stored by said third memory means 9, the fourth processing means 13 to execute the first process by using the expansion filter for digital image information yielded from the result of computing by the third processing means 12, the fifth processing means 14 to compute the differential values of respective sets of digital image information yielded from the results of computing by the second processing means 11 and the fourth processing means 13, and the fourth memory means 15 to store the result of computation by the fifth processing means 15. The embodiment of the detection apparatus 30 for an image defect, of the present invention is explained centering in a photomask like a reticle having a given pattern used for the manufacture of a semiconductor device. The image defect detecting apparatus and method of the present invention are not restricted to such embodiment, but naturally used for detecting defects of all images.

The data conversion means 2 of the present invention is not restricted to the constitution of the embodiment, but can be used in any constitutions, when shape of an inspection image of the photomask 1 can be detected to convert to digital image information.

The FIG. 1 shows the constitution in which an optical beam emitted from an arbitrary light source 4—for example, a laser beam—the one side of a photomask 1 loaded on an inspection stage 6 for image inspection processing is transmitted to the photomask 1, and the transmitted rays are received by an arbitrary photodetector 5.

In the present invention, all patterns—located in the photomask 1—can be inspected by that a thin laser beam is emitted from the light source 4 to scan freely, for example, a direction (e.g., Y direction), and simultaneously moves the inspection stage to the other direction (e.g., X direction.)

The photodetector may be assembled to move synchronizing with the laser.

In addition, in the present invention, the light source 4 used can be a size allowing simultaneous irradiation to the whole of the photomask 1, and light receiving means like one used for a CCD camera, for example, can be employed for the photodetector 5.

It is preferable that the data conversion means 2 of the present invention has analog/digital conversion means 3, for example.

In the present invention, digital image information converted by the data conversion means 2 is temporarily stored in the first memory means 7—a memory composed of an arbitrary composition—and in the following this step, digital image information stored in the first memory means 7 is copied and stored in both the second memory means 8 and the third memory means 9 by using an arbitrary copying means Furthermore, the filtering processes used in the present invention are expansion filter processing and a contraction filter processing. The filter used for the filter processing is so-called spatial filter 21 as shown in FIG. 2. The size of the filter is not specially limited. For example, 3×3 is generally usable as shown in FIG. 2. Various kinds of filters are employed according to shape of an image characteristics, etc., such as 8 adjacent system or 4 adjacent system.

As another example, 5×5 or 7×7 spatial filter can be similarly employed.

In the present invention, it is preferable to process internal brightness data of the information of digital image information.

For the expansion filter processing by using, for example, said spatial filter 21 made of 3×3 pixel in the present invention, the central pixel P (x, y) of the spatial filter 11 is selected for image inspection, and the data of the central pixel P (x, y) is replaced by the pixel data having the highest brightness data among pixel data including the pixel data of the central pixel data of the inspection pixel, i.e., its own pixel P (x, y,) and 8 pixels named "8 adjacent pixels" surrounding the own pixel.

This means that processing in the expansion filter processing is executed to increase light data.

On the other hand, reversely in the contraction filter processing, the data of the central pixel P (x, y) is replaced by the pixel data having the lowest brightness data among pixel data including the pixel data of the central pixel data of the inspection pixel, i.e., its own pixel P (x, y,) and 8 pixels named "8 adjacent pixels" surrounding the own pixel.

This means that processing in the contraction filter processing is executed to increase dark data.

The present invention is characterized by executing the second process—the contraction filter process—after executing the first process as the expansion filter process of the one of the identical digital image information, and reversely for the other identical digital image information, the first process—expansion filtering process—is executed after the earlier execution of the second process that is the contraction filtering process.

This means that the present invention allows finding accurately a defect part from the identical digital image information by applying such constitution.

Each only once processing can be executed for the process of the first processing and the second processing for the two identical digital image information. However, it is preferable that processing is repeated in a plurality of times.

The repeating frequencies are not always identical, but it is possible that the number of repeated execution of the first processing and the number of repeated execution of the second processing may be different.

However, it is desirable that the number of respective processing for different digital image information are coincident each other.

In the present invention, at least once of a pair of processes comprising the expansion filter processing and the contraction filter processing or a pair of processes comprising the contraction filter processing and the expansion filter processing is executed to the one of digital image information for inspection. The pair of these processes may be repeated in a plurality of frequencies. The following constitutions are possible as described in FIG. 3 stated later: for example, the contraction filter processing may be executed in a plurality of times after the expansion filter processing is executed in a plurality of times, or the expansion filter processing may be executed in a plurality of times after the contraction filter processing is executed in a plurality of times.

The present invention as stated before allows that the defect part in the inspection image of the photomask 1 is evidently detected by yielding a differential value through subtracting process of respective results of computation, after individual execution of reverse process to the identical digital image information.

The differential value is stored in the fourth memory means 15. It is possible that the presence or absence of the defect part of an image is evaluated by comparing a given standard value or an experience with the digital image information—stored in the fourth memory means—through reading arbitrarily by an operator. On the other hand, it is also possible that the presence or absence of the defect part of an image is automatically evaluated by comparing the standard value read from memory means 17, in which a given threshold value has been previously stored, using the comparing and evaluating means 16.

Further, the present invention allows to display and report the result of inspection with a suitable style on the basis of equipping an arbitrary displaying means 19 if necessary.

In the present invention, it is preferable that the first auxiliary memory means 22 is fitted between the first processing means 10 and the second processing means 11 in order to store temporarily the digital image information as the result of computation by the first processing means 10, and that the second auxiliary memory means 23 is fitted between the third processing means 12 and the fourth processing means 13 in order to store temporarily the digital image information as the result of computation by the third processing means 12.

Such constitution is necessary for storing temporarily the digital image information newly, that is made by the expansion filter processing or the contraction filter processing, in a auxiliary memory means 22 and 23 until the completion of processing of all pixels of the digital image information on the basis that the newly made digital image information differs from the original digital image information stored in the second memory means 8 and the third memory means 9 and that the newly processed digital image information restored in the second memory means 8 and the third memory means 9 is different in contents of the digital image information resulting in later difficult processing.

The next filter processing is executed by using the digital image information stored in the auxiliary memory means 22 and 23, and the result can be restored in the second or the third memory means 8 or 9 that are the original memory means.

This means that in the present invention as shown in FIG. 1, it is preferable that the first auxiliary memory means 22 is fitted between the first processing means 10 and the second processing means 11 in order to store temporarily the digital image information as the result of computation by the first processing means 10, and that the second auxiliary memory means 23 is fitted between the third processing means 12 and the fourth processing means 13 in order to store temporarily the digital image information as the result of computation by the third processing means 12.

Furthermore in the present invention, it is preferable that the third auxiliary memory means 24 is fitted between the second processing means 11 and the fifth processing means 14, and the fourth auxiliary memory means 25 is fitted between the fourth processing means and the fifth processing means.

The constitution of the fifth processing means—to compute a differential value—composed of the subtracting means used in the present invention is not specially restricted to allow to use conventionally known subtracting means.

Also further, the present invention has the comparing and evaluating means 16 for comparison of the digital image information made from the differential value stored in the fourth memory means 15 with a given standard value to evaluate the presence or absence of the defect part of an image and the displaying means 19 for displaying the output of the comparing and evaluating means 16. It is preferable that the standard value is stored in, for example, the fifth memory means 17.

In the present invention, displaying an image of said differential value allow to know not only the presence or absence of the defect part in the inspection image, but also the position and size of the defect part. Therefore, these kinds of information can be effectively used for correction of the inspection image in the later step.

In addition in the present invention, the information of image of said differential value could be that displaying the magnitude of differential values as the difference of lightness.

For instance, the magnitude of differential values can be represented with 256 brightness grades. The part of image of said differential value beyond the threshold value could be recognized as a defect part by corresponding of the magnitude of differential values to the brightness grades and by setting a given grade of the brightness as a threshold value.

Besides, Colored displaying of the image of said differential value allows easy recognition of a small image.

The present invention has a constitution in which as shown in FIG. 1, not only the output from the comparing and evaluating means 16, but also information from the first memory means 7 are inputted into the displaying means 19 via wiring L, and the positions in a coordinate on the image of the differential value can be simultaneously recognized to allow easy detection of the position of a defect.

The use of the spatial filter 21, for example, shown in FIG. 2 used in the present invention is effective for the analysis of the wiring pattern shapes composed of many lines of 0° or 90° or the shapes of cells.

However, A great part of pattern shapes actually used is composed of lines of 0° or 90°. Therefore, using the spatial filter 21 shown in FIG. 2 allows inspecting almost all of wiring patterns or cell shapes.

There are cases inappropriate to detect patterns having a rhombus or an oblique of 45° or 135°.

In such cases, it is necessary that 4 adjacent system is adopted by using the spatial filter 21 or that weighting is adjusted for respective pixels composing the spatial filter 21.

In addition, In an inspection image having a pattern with a peculiar oblique such as 22.5°, employing an appropriate spatial filter of a size of 5×5 or larger is required.

Even if such spatial filter is employed, weighting of respective pixels should be adjusted.

It is possible that an appropriate spatial filter of a size of 5×5 or larger is used for inspection of a wiring pattern composed of a pattern with having lines of 0° or 90° or a cell shape.

Such case provides an advantage of a shorter time of processing than the case of using a 3×3 spatial filter.

However, the filter processing in the present invention does not sometimes work well because of relation between the characteristics of the spatial filter used and the shape of inspection image.

In this case, when a certain detection method is employed using a certain spatial filter, a part having a pattern that is not detected by the filter processing is previously detected to store the information of its position in a sixth memory means 18; it can be set that when the address of the information of the position is detected, the filtering process is not executed.

It is also preferable in the present invention that the comparing and evaluating means 16 has a connection to a sixth memory means 18 storing a look-up table in which the information of a position of image site, where the evaluation of a defect is impossible, is previously stored according to a filter used.

In practice, a pattern is first made by mixing a pattern composed of lines of 0° or 90° with another pattern having oblique of such as 45° or 135° by CAD, etc.

There is not defect in the image produced by CAD.

Subsequently, an abnormal reaction appears in the position of the patterns of 45° or 135°, when the expansion processing or the contraction processing for an image information produced by CAD is executed by using the spatial filter 21—for example, a spatial filter shown in the FIG. 2—having an identical weighting to all pixels. It is known that the part in which such abnormal reaction has occurred is not the pattern of 0° or 90°. Therefore, it is the preferable constitution that the position is previously stored in the sixth memory means 18 or a proper memory means fitted in a CPU, and that in real execution of the expansion processing and the contraction processing, the position is covered by a mask to prohibit the execution of the process.

This means that in the present invention, two images with different properties are produced from a single image to solve a problem that the very small defect of the photomask—becoming higher in density and miniaturized—is difficult to detect because of such effect that an image deforms by a little vibration in photomask (reticle) inspection and real patterns do not always show a same size and a same shape even in the same photomask made by patterning of same design.

A concave defect is corrected with an expansion filter, for example, and on the other hand, a contraction filter is fitted to strengthen the concave defect. Such processing is carried out in a proper frequency followed by reverse filtering process of the same frequencies to recover the size of the image to the original one. In other words, twice expansion filter processes require twice contraction filter processes. The convex defect, concave defect, dots, and pinhole defect are all detectable by the combination of the expansion filter followed by contraction filter and the combination of the contraction filter followed by the expansion filter for a single image.

In these filtering processes, only the defect part is processed, a product without any defect is passed in the process, and a very small defect can be detected without an effect by the very small defect caused by said vibration and the dispersion of the product without any defect. Besides, there is a case requiring classifying the edge of the objective region of inspection in the group of angles before said filtering process. In this occasion, the filtering process should be effective to the angle group classified.

In the conventional defect detection method for the photomask, an image generated from identical pattern images and designed data located in separate positions of the identical photomask was used for comparison with the image actually collected from the photomask. Two images for comparison and reference should be always previously prepared; the very small defect can be difficultly detected because of an error caused by this step.

On the contrary, in the present invention, the error factor so far inhibited the detection of the very small defect has been removed by the reason the two images for comparison and reference are made from a single image collected from a real photomask by the filtering process. In addition, a simple comparison is allowed for the two images for comparison and reference that were originally identical image. A high speed process can be employed for the filtering process applied to the process to generate the two images for comparison and reference from a single image, the process to detect an edge angle carried out before the filtering process if necessary, and the process to detect the defect by yielding a differential image between comparing and referring images, due to their simple computing.

Figure 4A:
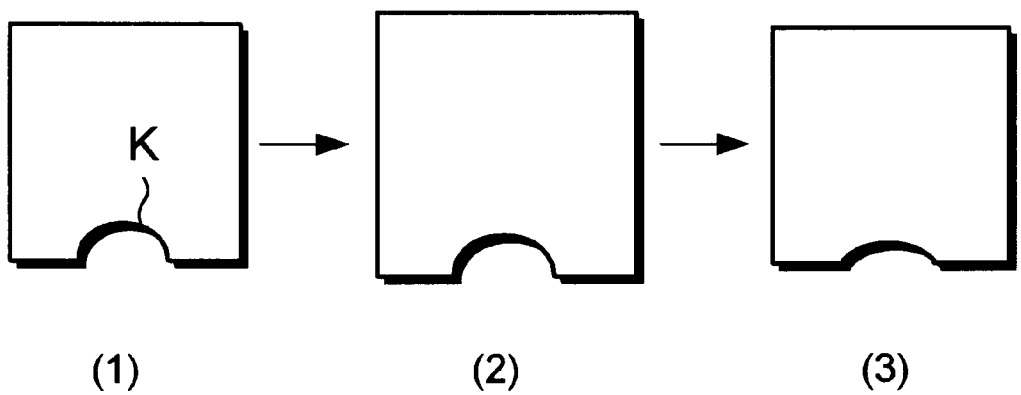
FIG. 4(A) and FIG. 4(B) are figures showing of an example of a change of image defect part in an image defect detection method of the present invention.

In the defect detecting method of the present invention, when an image defect part K exists in the inspection image of the photomask 1, as shown in FIG. 4, the digital image information is expanded by using the expansion filter that is the first processing means for the inspection image of the photomask 1 in (1) of FIG. 4(A) to deform the defect part K to considerably disappeared state as shown in (2) of FIG. 4(A) Subsequently, the digital image information shown in (2) of FIG. 4(A) is subjected to the contraction filter processing by using the contraction filter processing that is the second processing means to yield the state of a slightly deformed boundary shown in (3) of FIG. 4(A)

Figure 4B:
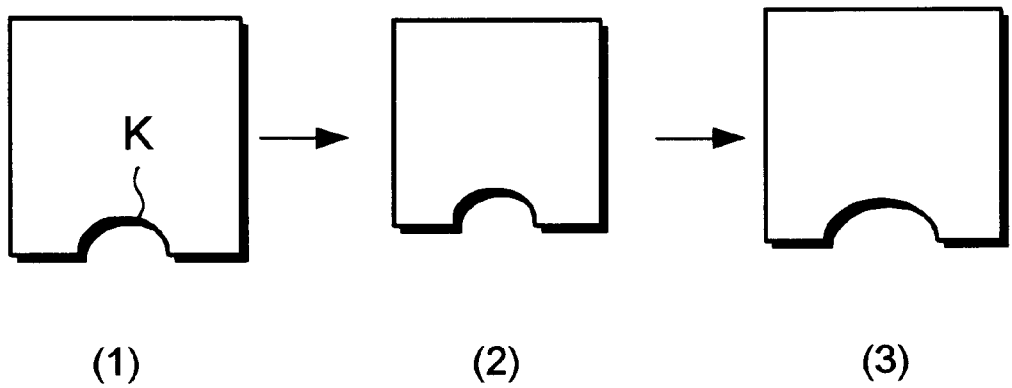

On the other hand, in (1) of FIG. 4(B), the contraction processing of the digital image information by using the contraction filter—the second processing means—for the digital image information 1 having the same defect part K as (1) of FIG. 4(A) increases the defect part K as shown in (2) of FIG. 4(B)

Subsequently, the digital image information is expanded by using the expansion filter that is the first processing means for the digital image information shown in the (2) of FIG. 4(B) to decrease the defect part K than shown in (2) of FIG. 4(B) as shown in (3) of FIG. 4(B)

Therefore, the differential value calculated from both sizes allows finding the presence of the defect part of the image.

Furthermore, it is required in the present invention that in detecting a digital image, the angles of edges are detected for a digital image information and the angles of respective edges are stored in a separate memory. A known filter may be employed for the detection of the edge.

The following filtering process is sometimes required for respective groups of angles classified by said angle detection. For example, edges are classified in groups such as 0, 90, 180, and 270° and 45, 135, 225, and 315° by using a filter of a proper size for detection of edges, and said filtering process may be carried out using filters effective on respective groups.

The constitution and performance of the detecting apparatus for the defect of the image, of the present invention are further described in detail with reference to FIG. 3.

For example, the photomask 1 set on the inspection stage 6 is aligned.

Next, The light 4 is irradiated on the upper surface of the photomask 1; the transmitted rays are received by a photodetector 5 to convert to a digital image data by an A/D converter 3.

In this time, the inspection stage 6 is controlled avoiding walk of an image that is being collected to move to the position for the next inspection.

The image (8 bits, gray scale) collected by these steps is stored in the first memory means 7. Besides, as shown in FIG. 3(A), the stored image is further replicated by the second memory means 8 and the third memory means 9.

The digital image information copied to the second memory means 8 is processed by the expansion filtering process using the first processing means 10, and the digital image information processed by the expansion filter is stored in the auxiliary memory means 22.

The digital image information stored in the auxiliary memory means 22 is again expanded by the expansion filtering process using the first processing means 10, and the digital image information is overwritten on the second memory means 8.

The digital image information stored in the second memory means 8 is processed by the contraction filtering process using the second processing means 11, and the digital image information prepared by the contraction is overwritten on the auxiliary memory means 22.

Subsequently, The digital image information stored in the auxiliary memory means 22 is again processed by the contraction filtering process using the second processing means 11, and the digital image information subjected to the contraction process is overwritten on the second memory means 8.

As the last memory means in the present embodiment, another memory means can be replaced to the second memory means 8 for use.

For the present embodiment, the following process is additionally carried out.

As shown in FIG. 3(B), the digital image information copied to the third memory means 9 is processed by the second processing means 12 using the contraction filter, and the digital image information processed by the contraction filter is stored in the auxiliary memory means 23.

The digital image information stored in the auxiliary memory means 23 is again contracted by the contraction filtering process using the second processing means 12, and the digital image information is overwritten on the third memory means 9.

The digital image information stored in the third memory means 9 is processed by the expansion filtering process using the first processing means 13, and the digital image information prepared by the expansion is overwritten on the auxiliary memory means 23.

Subsequently, The digital image information stored in the auxiliary memory means 23 is again processed by the expansion filtering process using the first processing means 13, and the digital image information subjected to the expansion process is overwritten on the third memory means 9.

As the last memory means in the present embodiment, another memory means can be replaced to the third memory means 9 for use.

Subsequently, the differential digital image information of the second memory means 8 and the digital image information of the third memory means 9 are prepared by the fifth processing means 14.

The brightness value of the differential digital image information obtained by this step is compared with the threshold value—previously set—evaluated as defect. For the part evaluated as the defect, a part corresponding to the defect in the photomask 1 is displayed on displaying means, such as a monitor, etc.

In the present invention, if an image quality is inferior, a noise may be removed within a necessary range at the time of said filtering process.

The image defect detection method in the present invention is given below.

As stated before, the image defect detecting method, as the second aspect of the present invention, to evaluate the presence or absence of the defect part in the given inspection image, comprises the step of: at least two duplicates are prepared from the digital image information of the inspection image obtained by digital processing of the inspection image; the first processing information is yielded by processing the first processing means using the expansion filter and the second processing means using the contraction filter in such order for the one copied digital image information; and also the second processing information is yielded by processing the second processing means using the contraction filter and the first processing means using the expansion filter in such order for the other copied digital image information; the differential value of the first processing information and the second processing information is computed; and presence or absence of an image defect in the inspection image is evaluated on the basis of the result.

In the defect detection method of the present invention, the first processing information and the second processing are preferably each once or repeated in a plurality of frequencies.

Further in the present invention, it is preferable that the differential values are compared with a given standard value previously determined to evaluate the presence or absence of an image defect in the inspection image.

Furthermore, in the defect detection method of the present invention, it is preferable that the presence or absence of an image defect in the inspection image is evaluated by referring to information about the presence of information—previously stored—of the position of an image site, where the defect of the image cannot be evaluated, according to the kind of the filter used for the inspection.

Figure 10:
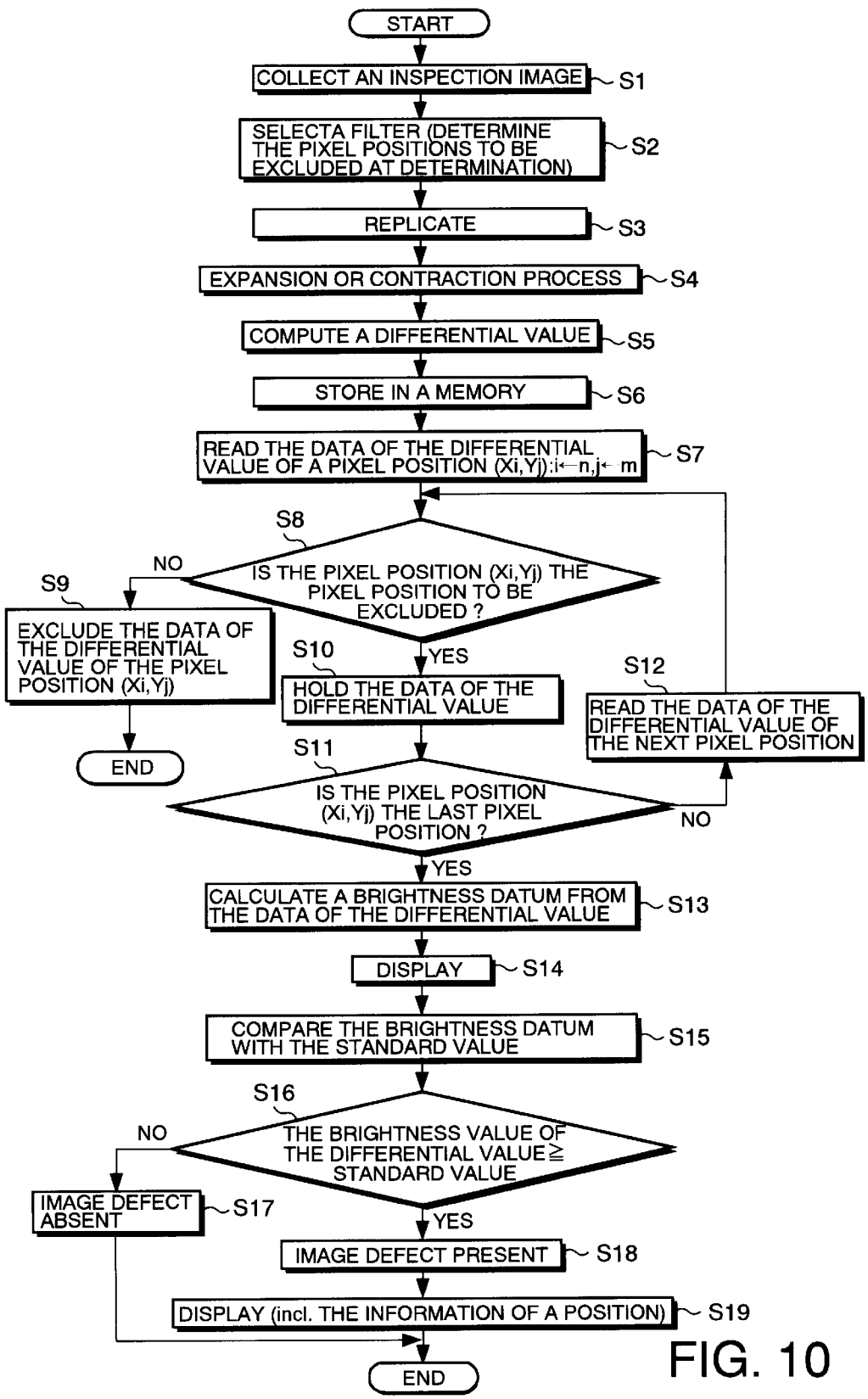
FIG. 10 is a flow chart showing operational steps in an embodiment of the detection method of the present invention for an image defect.

In this occasion, an embodiment of the data processing method related to the selection of a filter and an embodiment of the comparing step of a differential value with a proper standard value in the present invention are described with reference to the flow chart of FIG. 10.

First after starting, the inspection image is collected in the step (S1), a filter suitable to the inspection image is selected in the step (S2), the information about the pixel position, in which the defect part of the image cannot be detected, inappropriate for process with the filter selected is previously determined, and the position is stored in, for example, the sixth memory means 18 in FIG. 1.

Subsequently, a copied image information is prepared from the inspection image information in the step (S3), said expansion or contraction filtering processes is executed in the step (S4), the differential value from two sets of image information is computed by the computing means 14 in process of said expansion or contraction filter in the step (S5), and the result is stored by the fourth memory means 15 in the step (S6).

Following these steps, the differential value stored by the fourth memory means 15 is read by the evaluating means 16 of the FIG. 1 in the step (S7) in the order of the position of pixels, it is evaluated whether the pixel position of the data of the differential value read serially corresponds to the pixel position—previously stored—necessary of exclusion in the step (S8), and if the data of positions of the differential value—(i=n, j=m in (Xi, Yj))—read correspond to the pixel position to be excluded, the data are excluded in the subsequent steps of process in the step (S9).

Further, if the data of positions of the differential value read do not correspond to the pixel position to be excluded, the differential value is kept in the step (S10).

Next, in the step (S11), the differential value of an inspection image read is evaluated whether it is the last one or not; if no, the data are transferred to the step (S12) to select and read the next differential value, the data of the x position is increased for 1 (if the position is the last x position, the y position is increased for 1, and the x position is set to first x position) to move back the step (S8), and said previous operations are repeated.

Finally, if the data of the differential value is the last data in the step (S11), all the differential values held are converted to brightness data in the step (S13), on the situation, the data are displayed by the display means 19 in the step (S14) to compare with the standard value (previously assigned as the threshold value) stored in the fifth memory means 17 in the step (S15), in the step (S16), if the brightness data yielded from the differential values are smaller than the standard value of the brightness data, the step (S17) evaluates the inspection image as having no defect part to make the end. On the other hand, in the step (S16), the brightness data yielded from the differential values are larger than the standard value of the brightness data, the step (S18) evaluates the inspection image as having a defect part to make the end by displaying the differential values together with the information of the position by the display means 19 in the step (S19).

The another aspect of the present invention of the image defect detecting method comprises the step of: the first step converting an inspection image to a digital image; the second step storing the digital image information to the first memory means; the third step storing the digital image information stored in the first memory means in respective second memory means and third memory means; the fourth step executing the first processing by using the expansion filter for the digital image information stored in the second memory means; the fifth step executing the second process by using the contraction filter for the digital image information obtained from the fourth step; the sixth step executing the second process by using the contraction filter for the digital image information stored in the third memory means; the seventh step executing the first process by using the expansion filter for the digital image information obtained from the sixth step; the eighth step computing the differential value based on respective sets of processing information obtained in the fifth and seventh steps; the ninth step storing the differential value obtained from the eighth step in the fourth memory means.

In said steps, a proper repetition of the fourth step and fifth step is preferable. Besides, a proper repetition of the sixth step and seventh step is also preferable.

In the present invention, it is preferable that the tenth step is also included to evaluate the presence or absence of an image defect in the inspection image by comparing the differential value with the given standard value previously determined.

Also in the present invention, in the tenth step, the eleventh step is also included to refer to information in which the information of position of image site—previously stored—for which the defect of the image cannot be evaluated according to the kind of a filter used in the inspection.

Although the number of repetition of the first process using the expansion filter and the second process using the contraction filter in the present invention are not specially restricted, may be restricted according to size and interval of patterns in the inspection image. Particularly in the contraction process, when the process causes an occurrence of a part in which abutted patterns contact or overlap each other, a subsequent processing becomes difficult. In this point of view, the number of repetition of respective processes are restricted.

Although the standard of selecting the spatial filter used for the present invention is not specially restricted, an appropriate filter can be preferably selected from information about the wiring pattern in the inspection image, or shape, size, interval between them, or the angle of constitution pattern (instance of 0° or 90° patterns, 45° or 135° patterns, or other patterns such as 22.5° pattern) of cells, etc.

Furthermore, the distribution of weighting in respective pixel parts of the spatial filter selected, said repetition frequencies, etc. are naturally considered for selection.

Therefore, preferably, a look-up table is prepared to designate the relationship between given patterns and the spatial filter used on the basis of the results of a number of simulation, in order to make easy and automated selection of the spatial filter possible.

Next, another aspect of the image defect detection method of the present invention, is described below.

Currently in the relation with present embodiment, the size of the defect necessary for detection is increasingly becoming smaller according to miniaturization of patterns. For instance, a defect caused by incorrect size or a defect caused by walk of a position is very difficult to detect.

Figure 5:
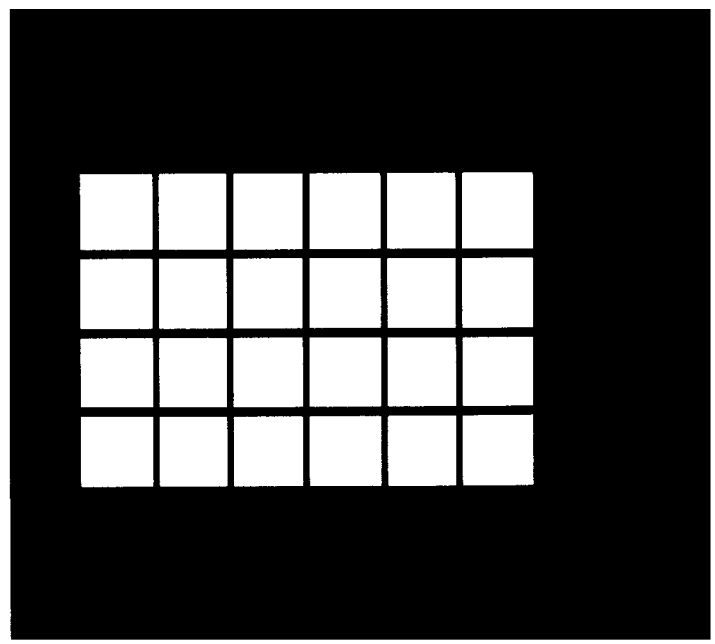
FIG. 5 is a figure showing a constitutional example of a CAD pattern of a normal form used in another embodiment of an image defect detection method of the present invention.
Figure 6:
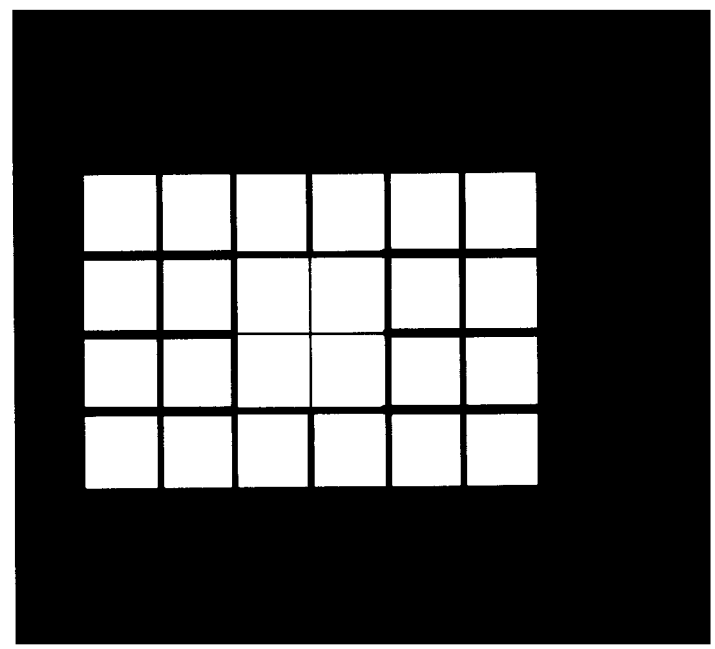
FIG. 6 is a figure showing a constitutional example of a pattern form of an image having a defect part prepared from a CAD pattern in the FIG. 5.

For example, when four cells in the central part in the pattern are larger than surrounding patterns, for example as shown in FIG. 6, the detection of defect is difficult by the conventional detecting method for image defect in the requirement of a pattern having a plurality of a normal shape of cells made by using CAD as shown in FIG. 5.

However, using the detecting method for image defect of the present invention allows detecting effectively and accurately the defect of the image.

Figure 7A:
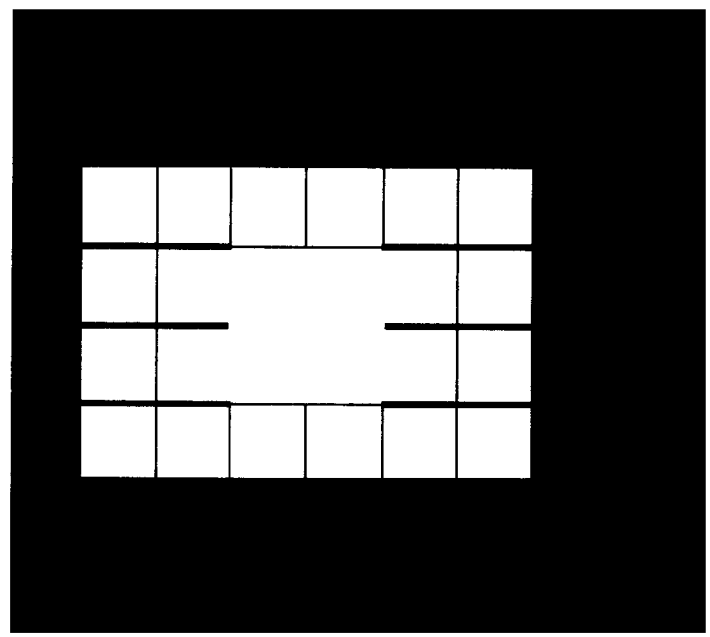
FIG. 7(A) and FIG. 7(B) are figures showing the results of operation in another embodiment in an image defect detection method of the present invention.
Figure 7B:
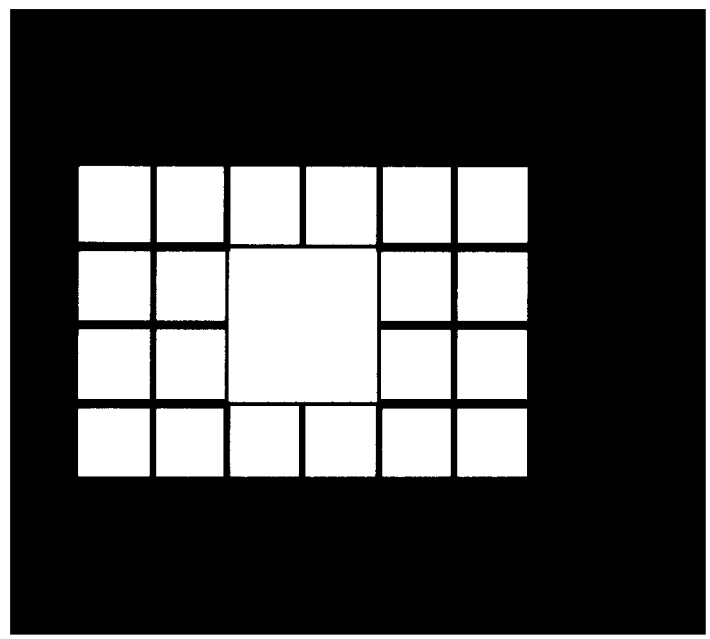

This means that the image datum as shown in FIG. 7(B) is yielded by execution of the second process using the similar contraction filter to said one, after an image datum shown in FIG. 7(A) is yielded by executing the aforementioned first process by using an expansion filter—a spatial filter shown in FIG. 2—for data of images having a defect part shown in FIG. 6.

Figure 8A:
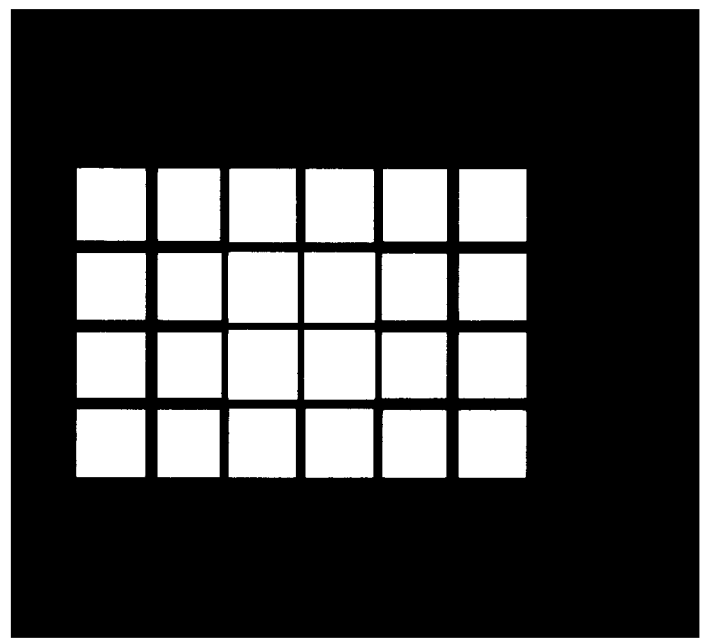
FIG. 8(A) and FIG. 8(B) are figures showing the results of operation in another embodiment in an image defect detection method of the present invention.
Figure 8B:
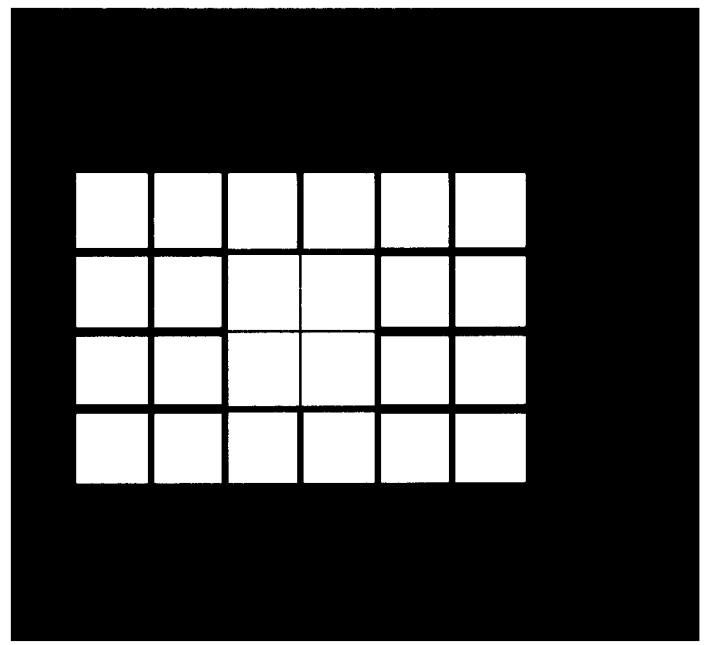

On the other hand, the image datum as shown in FIG. 8(B) is yielded by execution of the first process using the similar expansion filter to said one, after an image datum shown in FIG. 8(A) is yielded by executing the second process by using the similar contraction filter to said one for the identical data of images having the identical defect part shown in FIG. 6.

In the present embodiment, the defect of a large size is connected to surrounding patterns by early process with the expansion filter for the image data. Thus, the later process with the contraction filter does not recover the connected part to the original one.

Figure 9:
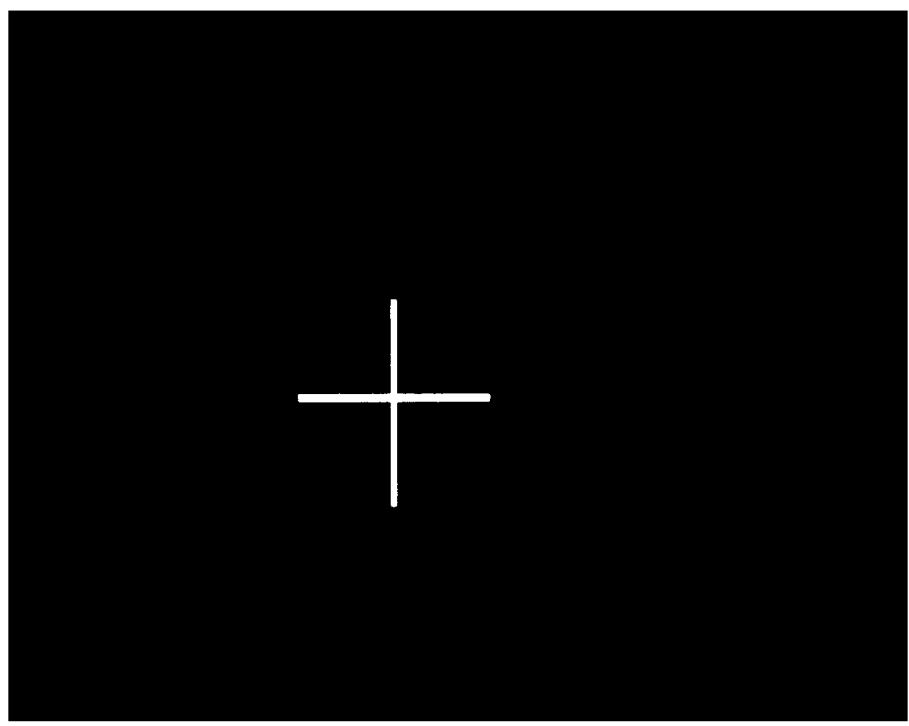
FIG. 9 is a figure showing the results of operation in another embodiment in an image defect detection method of the present invention, and a pattern figure made based on the differential value between the FIG. 7(B) and the FIG. 8(B)

On the other hand, the shape of the connected part does not disappear by the early process with the contraction filter for the image data having the defect part even if later process with the expansion filter. Therefore, the position of the defect part in such image shown in FIG. 9 is displayed by computing the differential value of the image data shown in FIG. 7(B) and FIG. 8(B).

The present invention has the effect that easy detection is possible for not only the image defect of such incorrect size, but also the image defect based on the walk of position.

Next, other embodiment of the image defect detection apparatus and method of the present invention are described in detail with reference to FIG. 11.

The embodiment described above, copies a single inspection image, and prepares image data from respective copied inspection images subjected to the expansion filtering process followed by the contraction filtering process and from those subjected to the contraction filtering process followed by the expansion filtering process to make computing the differential value of the both to the basic designing concept. However, in the present embodiment, a comparison is carried out for an image data yielded from the original inspection images subjected to any one of the expansion filtering process followed by the contraction filtering process or the contraction filtering process followed by the expansion filtering process with the original inspection image to compute differential value of them.

Specifically, an image defect detection apparatus comprises a means to make replicated inspection images from a single inspection image, the first image processing means to carry out an image processing applying an expansion filter and a contraction filter in this order to the replicated inspection images, an image processing applying a contraction filter and an expansion filter in this order, or the repetition of the image processing in a plurality of frequencies, and a means to output image information to output image information made from differential values of image information outputted from said first image processing means and the inspection image, and a method for the detection of an image defect, comprising a step of preparing a single inspection image, a step to make replicated inspection images from the inspection image, the first image processing step to carry out an image processing applying an expansion filter and a contraction filter in this order to the replicated inspection images, an image processing applying a contraction filter and an expansion filter in this order, or the repetition of the image processing in a plurality of frequencies, and a step of computing the differential value to compute the differential value and a step to output image information to output image information made from the differential value on the basis of the comparison of an image information outputted from said first image processing means with the inspection image.

In the present embodiment, the original image data of the inspection image stored in the first memory means 7 is copied by the copying means 20. The same image processing as that of the first image processing means A—described in the FIG. 1—is carried out for the copied image data to compare the result with the original image data of the inspection image stored in the first memory means 7. The differential value is known by computing with the computing means 26. Later data processing is subjected to the same processing as that of the processing shown in FIG. 1 and explained before.

Figure 11:
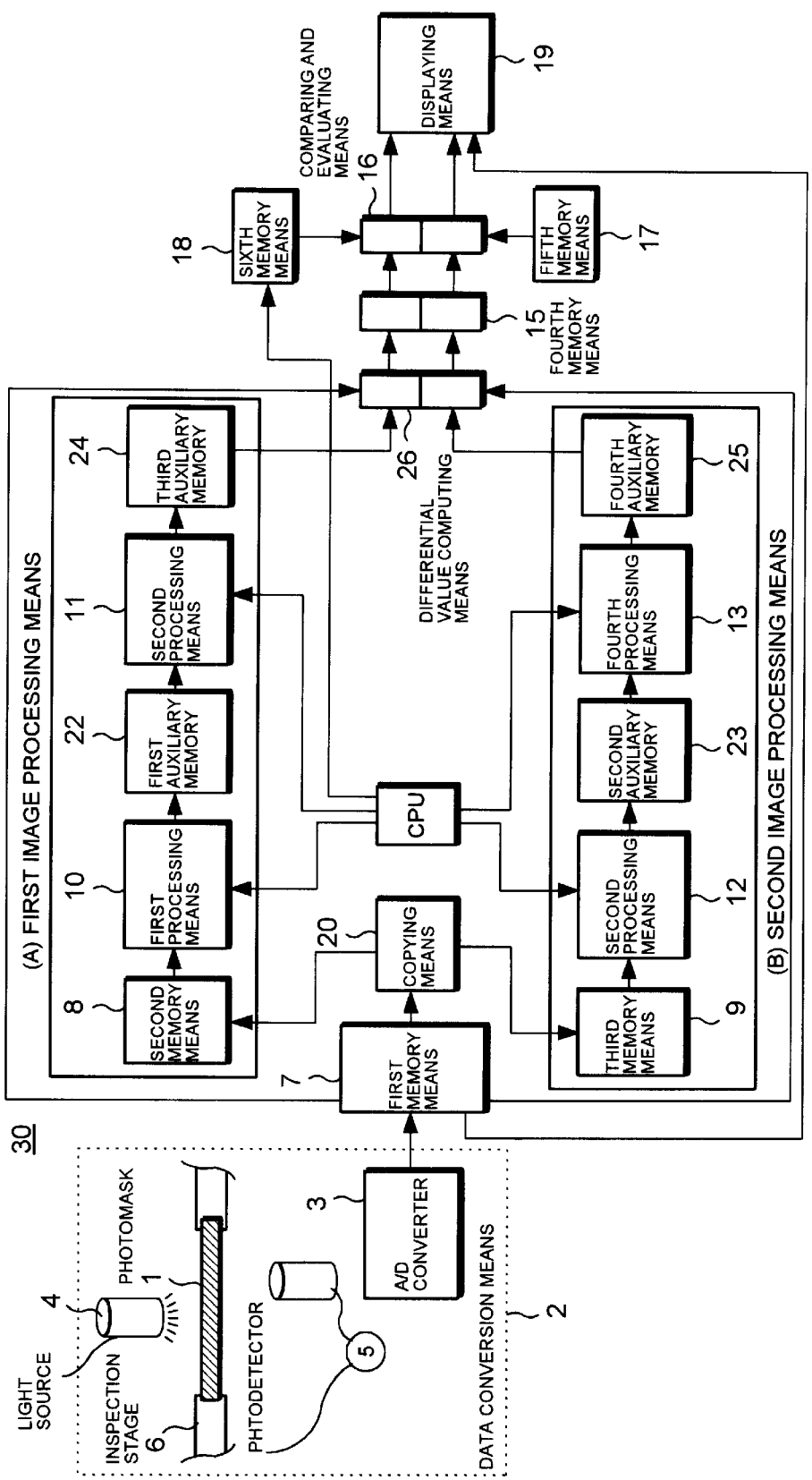
FIG. 11 is a block diagram showing an example of an apparatus for practicing the method of another embodiment in the method of the present invention of the detection of an image defect.

Thus, the image data (1) of the original inspection image, shown in the FIG. 4(A), is compared with the image data (3), shown in FIG. 4(A), processed with the first image processing means A, shown in FIG. 11, to compute differential value thereof.

Similarly, the original image data of the inspection image stored in the first memory means 7 is copied by the copying means 20. The same image processing as that of the second image processing means B—shown in FIG. 1—is carried out for the copied image data to compare the result with the original image data of the inspection image stored in the first memory means 7. The differential value is known by computing with the computing means 26. Later data processing is subjected to the same processing as that of the processing shown in FIG. 1 and explained before.

Thus, the image data (1) of the original inspection image, shown in FIG. 4(B), is compared with the image data (3), shown in FIG. 4(B), processed with the second image processing means B to compute differential value thereof.

The differential value yielded by such method shows very small difference from said embodiment to provide a satisfactory applicability.

In addition, a further other aspect of the present invention is a recording medium in which a program is recorded to execute the following processes related to a method for detecting an image defect by a computer, comprising the step of: in the method for detection of a defect to evaluate the presence or absence of the defect image in the given inspection image, at least two duplicates are prepared from the digital image information of the inspection image obtained by digital processing of the inspection image; the first processing information is yielded by processing the first processing means using the expansion filter and the second processing means using the contraction filter in such order for the one copied digital image information; and also the second processing information is yielded by processing the second processing means using the contraction filter and the first processing means using the expansion filter in such order for the other copied digital image information, and the differential value of the first and second processing information is computed; and the presence or absence of an image defect in the inspection image is evaluated on the basis of the result. As described, the present invention has the effect allowing speedy inspection without any effect of the dispersion—a cause of occurrence of a false defect in the inspection of a photomask (reticle) used in, for instance, semiconductor preparation—of product passed in a test. Furthermore, the present invention, as stated before, an inputted digital image information is respectively reproduced (copied) in two memories, contradictory filter processing is carried out for information of these two digital images in proper frequencies, a differential digital image information is made from the information of these two digital images, a pixel showing a threshold or higher value, if it is evaluated as a defect in the differential digital image information, is determined as a defect, and finally the objective part of the original digital image information taken is displayed on a monitor, etc.

As described in several aspects and preferred embodiments, in the present invention, the problem of the dispersion of products passed in a inspection can be neglected, because the information of the two digital images for final image comparison in the present invention is derived from the identical digital image information. Besides, in the present invention, two sets of digital image information are prepared from the identical digital image information of the inspection object; therefore, accurate positioning (alignment process) of two sets of digital image information such as digital image information for comparison and reference immediate before the inspection—exemplified by the die-to-die and die-to-database—is not necessary. Finally, the algorithm of the inspection of the present invention is made by the combination of simple filtering processes to allow inspecting a very small defect speedier than a conventional inspection apparatus.

What is claimed is:

1. An image defect detection apparatus comprising:
   a means for making two copied inspection images from a single inspection image;
   a first image processing means for applying an expansion filter and a contraction filter to the one copied inspection image in this order;
   a second image processing means for applying a contraction filter and an expansion filter to the other copied inspection image in this order; and
   a means for outputting image information made from differential image information of image information outputted from said respective first image processing means and second image processing means.

2. An image defect detection apparatus according to claim 1, wherein said expansion filter and said contraction filter include a spatial filter.

3. An image defect detection apparatus according to claim 2, wherein said spatial filter is made of n×n pixels (n: odd integer).

4. An image defect detection apparatus according to claim 3, wherein said expansion filter including said spatial filter replaces data of a center pixel with data of a pixel having the highest brightness data in n×n pixels.

5. An image defect detection apparatus according to claim 3, wherein said contraction filter including said spatial filter replaces data of a center pixel with data of a pixel having the lowest brightness data in n×n pixels.

6. An image defect detection apparatus comprising:
   a means for making two copied inspection images from a single inspection image;
   a first image processing means comprising an expansion processing means executing expansion process for the one of the copied inspection image by using an expansion filter and a contraction processing means executing a contraction process for the inspection image treated by the expansion processing by using a contraction filter;
   a second image processing means comprising a contraction processing means executing contraction process for the other of the copied inspection image by using a contraction filter and an expansion processing means executing an expansion process for the inspection image treated by the contraction processing by using an expansion filter; and a means for outputting image information to display a defect part, outputting image information being composed of a differential image information of respective sets of image information outputted from the first and the second image processing means.

7. An image defect detection apparatus according to claim 6, wherein said expansion filter and said contraction filter include a spatial filter.

8. An image defect detection apparatus according to claim 7, wherein said spatial filter is made of n×n pixels (n: odd integer).

9. An image defect detection apparatus according to claim 8, wherein said expansion filter including said spatial filter replaces data of a center pixel with data of a pixel having the highest brightness data in n×n pixels.

10. An image defect detection apparatus according to claim 8, wherein said contraction filter including said spatial filter replaces data of a center pixel with data of a pixel having the lowest brightness data in n×n pixels.

11. A image defect detection apparatus comprising:
   a data conversion means for converting the inspection image to digital image information;
   a first memory means for storing said digital image information outputted from said data conversion means;
   a second memory means and the third memory means for storing digital image information copied from said digital image information individually;
   a first processing means to execute the first process by using an expansion filter for digital image information stored by said second memory means;
   a second processing means to execute the second process by using a contraction filter for digital image information yielded from the result of computing by the first processing means;
   a third processing means to execute the second process by using a contraction filter for digital image information stored by said third memory means;
   a fourth processing means to execute the first process by using the expansion filter for digital image information yielded from the result of computing by the third processing means;
   a fifth processing means to compute the differential image information of respective sets of digital image information yielded from the results of computing by the second processing means and the fourth processing means; and
   a fourth memory means to store the result of computation by the fifth processing means.

12. An image defect detection apparatus according to claim 11, wherein said expansion filter and said contraction filter include a spatial filter.

13. An image detection apparatus according to claim 12, wherein said spatial filter is made of n×n pixels (n: odd integer).

14. An image defect detection apparatus according to claim 13, wherein said expansion filter including said spatial filter replaces data of a center pixel with data of a pixel having the lowest brightness data in n×n pixels.

15. An image defect detection apparatus according to claim 13, wherein said contraction filter including said spatial filter replaces data of a center pixel with data of a pixel having the lowest brightness data in n—n pixels.

16. An image defect detection method comprising:
   a step of preparing two replicates of inspection image from a single inspection image;
   a first image processing step of processing an image using the expansion filter and the contraction filter in such order for the one of replicated inspection images;
   a second image processing step of processing an image using the contraction filter and the expansion filter in such order for the other of replicated digital image information; and
   a step of outputting image information composed of the differential information that is computed from image information respectively outputted from the first image processing step and the second image processing step.

17. An image defect detection method according to claim 16, wherein said expansion filter and said contraction filter include a spatial filter being made of n×n pixels (n: odd integer) and said first and second image processing steps include
   an expansion step of replacing data of a center pixel with data of a pixel having the highest brightness data in n×n pixels; and
   a contraction step of replacing data of a center pixel with data of a pixel having the lowest brightness data in n×n pixels.

18. An image defect detection method for determining presence or absence of an image defect in a given inspection image, comprising the steps of:
   making at least two image copies from the digital image information of the inspection image obtained by digital processing of the inspection image;
   yielding a first processing information by processing a first processing means using an expansion filter and a second processing means using a contraction filter in such order for the one copied digital image information; and
   yielding a second processing information by processing a second processing means using a contraction filter and a first processing means using an expansion filter in such order for the one copied digital image information;
   computing a differential information of the first processing information and the second processing information; and
   evaluating a presence or an absence of an image defect in the inspection image from the differential information.

19. An image defect detection method according to claim 18, wherein the first process and the second process are repeated once or in a plurality of times in respective steps.

20. An image defect detection method according to claim 18, wherein the expansion process by using the expansion filter and the contraction process by using the contraction filter in the first processing information yielding step are repeated in a plurality of times in combination of these operation steps; and
   the contraction process by using the contraction filter and the expansion process by using the expansion filter in the second processing information yielding step are repeated in a plurality of times in combination of these operation steps.

21. An image defect detection method according to claim 19, wherein the number of the repetition of the first process and the second process are identical in respective steps.

22. An image defect detection method according to claim 18, wherein said expansion filter and said contraction filter include a spatial filter being made of n×n pixels (n: odd integer) and said first and second processing information yielding steps include an expansion step of replacing data of a center pixel with data of a pixel having the highest brightness data in n×n pixels; and a contraction step of replacing data of a center pixel with data of a pixel having the lowest brightness data in n×n pixels.

23. An image defect detection method comprising:

a first step of converting an inspection image to a digital image;

a second step of storing the digital image information to a first memory means;

a third step of storing the digital image information stored in the first memory means in respective second memory means and third memory means;

a fourth step of executing a first processing by using a expansion filter for the digital image information stored in the second memory means;

a fifth step of executing a second process by using a contraction filter for the digital image information obtained from the fourth step;

a sixth step of executing the second process by using the contraction filter for the digital image information stored in the third memory means;

a seventh step of executing the first process by using the expansion filter for the digital image information obtained from the sixth step;

a eighth step of computing a differential information based on respective sets of processing information obtained in the fifth and seventh steps; and a ninth step of storing the differential information obtained from the eighth step in the fourth memory means.

24. An image defect detection method according to claim 23, wherein the fourth step and fifth step are repeated in a plurality of times.

25. An image defect detection method according to claim 23, wherein the sixth step and seventh step are repeated in a plurality of times.

26. An image defect detection method according to claim 23, wherein said expansion filter and said contraction filter include a spatial filter being made of n×n pixels (n: odd integer) and said fourth and seventh steps include an expansion step of replacing data os a center pixel with data of a pixel having the highest brightness data in n×n pixels; and said fifth and sixth steps include a contraction step of replacing data of a center pixel with data of a pixel having the lowest brightness data in n×n pixels.

* * * * *